(12) United States Patent
Zhang

(10) Patent No.: US 8,165,821 B2
(45) Date of Patent: Apr. 24, 2012

(54) SYSTEM AND METHODS FOR INDEL IDENTIFICATION USING SHORT READ SEQUENCING

(75) Inventor: Zheng Zhang, Pasadena, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 800 days.

(21) Appl. No.: 12/026,477

(22) Filed: Feb. 5, 2008

(65) Prior Publication Data

US 2008/0189049 A1 Aug. 7, 2008

Related U.S. Application Data

(60) Provisional application No. 60/888,196, filed on Feb. 5, 2007.

(51) Int. Cl.
*G01N 33/48* (2006.01)
*C12Q 1/68* (2006.01)
*G06G 7/58* (2006.01)
*G06F 7/60* (2006.01)

(52) U.S. Cl. .................. 702/19; 435/6; 702/20; 703/2; 703/11

(58) Field of Classification Search .................. None
See application file for complete search history.

(56) References Cited

U.S. PATENT DOCUMENTS

| | | | |
|---|---|---|---|
| 5,891,632 A | 4/1999 | Imai | |
| 6,054,276 A | 4/2000 | Macevicz et al. | |
| 6,223,127 B1 | 4/2001 | Berno | |
| 6,223,175 B1 | 4/2001 | George et al. | |
| 6,401,043 B1 | 6/2002 | Stanton et al. | |
| 6,714,874 B1 | 3/2004 | Myers et al. | |
| 6,785,614 B1 | 8/2004 | Collins et al. | |
| 6,895,337 B1 | 5/2005 | Scholl et al. | |
| 7,313,555 B2 | 12/2007 | Klier | |
| 2003/0211504 A1 | 11/2003 | Fechtel et al. | |
| 2006/0024681 A1 | 2/2006 | Smith et al. | |

FOREIGN PATENT DOCUMENTS

WO WO-2008/098014 8/2008

OTHER PUBLICATIONS

Shendure et al., Science, vol. 309, pp. 1728-1732, 2005.*
Chiu et al., "PET-Tool: a software suite for comprehensive processing and managing of Paired-End diTag (PET)sequence data," *BMC Bioinformatices*, Biomed Central, London, GB, (Aug. 25, 2006)vol. 7, No. 1, pp. 390.
International Application No. PCT/US2008/053101 for International Search Report and Written Opinion of the ISA dated Mar. 23, 2009.
Tuzun et al., "Fine-scale structural variation of the human genome," *Nature Genetics*, (Jul. 2005) vol. 37, No. 7, pp. 727-732.
U.S. Appl. No. 12/026,477, Office Action Mailed on Oct. 8, 2010.
PCT/US2008/053101, , "International Preliminary Report on Patentability/Written Opinion", Aug. 11, 2009 , pp. 1-7.
Chaisson et al., "Fragment assembly with short reads," *Bioinformatics*, (2004) vol. 20 No. 13, pp. 2067-2074.
Dew et al., "A Tool for Analyzing Mate Pairs in Assemblies (TAMPA)," *Journal of Computational Biology*, (Nov. 5, 2005) vol. 12 No. 5, pp. 497-513.
Metzker, Michael L., "Emerging technologies in DNA sequencing," *Genome Research*, (2005) pp. 1767-1776.
She et al., "Shotgun sequence assembly and recent segmental duplications within the human genome," *Nature*, (Oct. 21, 2004) vol. 431, pp. 927-930.
Warren et al., "Assembling millions of short DNA sequences using SSAKE," *Bioinformatics*, (2007) vol. 23 No. 4, pp. 500-501.
Whiteford et al., "An analysis of the feasibility of short read sequencing," *Nucleic Acids Research*, (2005) vol. 33 No. 19, pp. 1-6.

\* cited by examiner

*Primary Examiner* — Shubo Zhou

(57) ABSTRACT

Systems, methods, and analytical approaches for short read sequence assembly and for the detection of insertions and deletions (indels) in a reference genome. A method suitable for software implementation is presented in which indels may be readily identified in a computationally efficient manner.

20 Claims, 8 Drawing Sheets

DELETION

INSERTION

Exemplary Size Range For Indels

Figure 1:
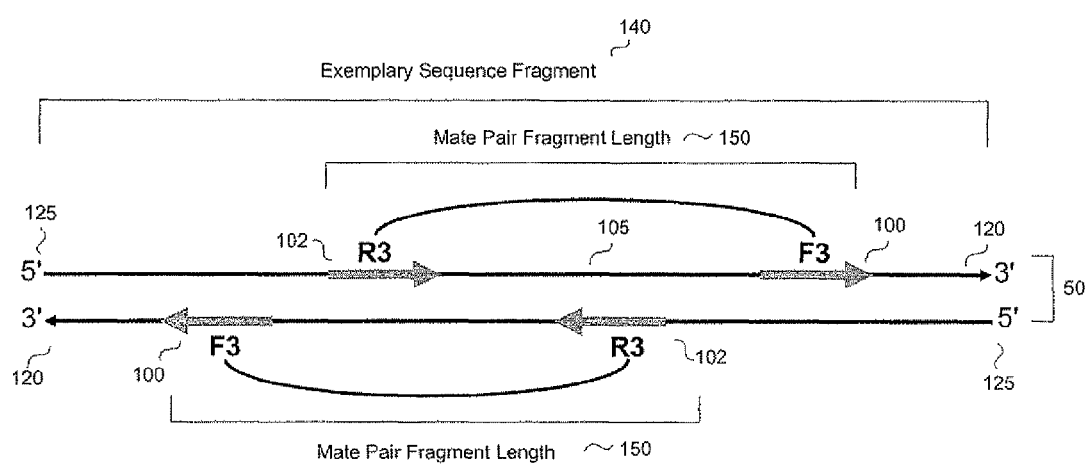

Large Size Insertion / Deletion – Approx 0.2 Kb or greater

Medium Size Insertion / Deletion – Approx 10 bp to 0.2 Kb

Small Size Insertion / Deletion – Approx 1 bp to 10 bp

Small / Medium Indel Identification
Using Window / Search Region Scanning

Exemplary Validation / Simulations

TABLE 1
False Positive Rates for Deletions

| m | D | FP |
|---|---|---|
| 1 | 2 | 7.2E-5 |
| 1 | 20 | 2.75E-4 |
| 0 | 20 | 5.4E-5 |
| 0 | 50 | 6.3E-5 |
| 0 | 100 | 7.5E-5 |

TABLE 2
False Positive Rates for Insertions

| m | I | FP |
|---|---|---|
| 1 | 5 | 4.1E-4 |
| 0 | 5 | 7.5E-5 |
| 0 | 8 | 1.17E-4 |

FIGURE 6

SYSTEM AND METHODS FOR INDEL IDENTIFICATION USING SHORT READ SEQUENCING

CROSS REFERENCE TO RELATED APPLICATIONS

This application claims priority to U.S. Provisional Patent Application Ser. No. 60/888,196, filed Feb. 5, 2007 and entitled "Finding Indels Using Short Sequencing Reads", the entire contents of which are hereby incorporated by reference.

FIELD

The present teachings generally relate to systems, methods, and software for analyzing sequence data and more particularly to systems, methods, and software for resequencing and identifying insertions/deletions using short read sequence data.

INTRODUCTION

High-throughput short read nucleic acid sequencing approaches continue to rapidly evolve and provide the potential for several orders of magnitude more sequence throughput than conventional Sanger sequencing methods. Platforms and instrumentation capable of generating short read sequence information include by way of example; Applied Biosystems SOLiD instrument platform, Solexa/Illumina 1G genome analysis system and others. Such systems typically produce vast quantities of sequence information with comparatively short lengths (on the order of approximately 10-50 based pairs) relative to Sanger-based approaches (approximately 500-1000 base pairs). Exemplary applications of high-throughput short read nucleic acid sequencing approaches include resequencing, gene expression analysis, and genomic profiling. One difficulty in utilizing data from short read sequencing platforms is that modern assembly programs, data analysis approaches, and error correction routines have been designed to operate with the longer read lengths found in conventional Sanger-based approaches and are not well suited for assembly of short read sequence information. For example, one difficulty which is encountered when attempting to adapt conventional sequence analysis approaches to short read sequence information is that as the length of each individual read decreases, the probability that a read will occur more than once within a reference sequence increases. Additionally, complex genomes, such as mammalian genomes, often contain many repetitive sequences and it becomes increasingly challenging to assemble or relate short read information to the underlying or reference sequence. Thus a significant challenge in interpreting and analyzing short read sequence information relates to mapping this information to a relatively large genome while reducing the number of errors and false alignments.

SUMMARY

The present teachings are directed to systems, methods, and analytical approaches for interpreting short read sequence information including nucleic acid fragment assembly. In one aspect, the present teachings may be adapted for use in nucleic acid resequencing applications where relatively large amounts of short read sequence information is available and to be analyzed using reference sequence information. The methods described herein may advantageously be used to identify and locate putative insertions and deletions (e.g. indels) with respect to a reference sequence or genome. The analysis approaches described herein further reduce the time and computational complexity when allowing for indels within a reference sequence or genome. Additionally, the present teachings may be adapted to reduce the number of false alignments and mapping errors arising when mapping short read sequence data to reference sequence data.

In various embodiments, a method of nucleic acid sequence analysis is taught. The method comprising the steps of: receiving nucleic acid sequence information comprising one or more mate pair sequences, wherein mate pair sequences comprise non-overlapping pairwise sequences separated by an intervening sequence length; receiving nucleic acid sequence information comprising at least one reference sequence; performing a mapping operation for each of the one or more mate pair sequences in which the non-overlapping pairwise sequences are aligned to the at least one reference sequence by the steps of: performing a first mapping operation aligning the non-overlapping pairwise sequences to the at least one reference sequence with a selected mismatch constraint identifying non-overlapping pairwise sequences for which one of the non-overlapping pairwise sequences align to the at least one reference sequence while satisfying the selected mismatch constraint; performing a second mapping operation designating a window region of the reference sequence to align the non aligned pairwise sequence with a selected mismatch constraint; identifying non-overlapping pairwise sequences that are successfully mapped following performing the first and second mapping operations; and, outputting the results of the mapping operations.

In other embodiments, a system for nucleic acid sequence analysis is taught. The system further, comprising: a data analysis unit configured to: receive nucleic acid sequence information for one or more mate pair sequences, wherein mate pair sequences comprise non-overlapping pairwise sequences separated by an intervening sequence length and further configured to receive nucleic acid sequence information for at least one reference sequence; perform a mapping operation for each of the one or more mate pair sequences in which the non-overlapping pairwise sequences are aligned to the at least one reference sequence by the steps of: performing a first mapping operation aligning the non-overlapping pairwise sequences to the at least one reference sequence with a selected mismatch constraint identifying non-overlapping pairwise sequences for which one of the non-overlapping pairwise sequences align to the at least one reference sequence while satisfying the selected mismatch constraint; performing a second mapping operation designating a window region of the reference sequence to align the non aligned pairwise sequence with a selected mismatch constraint; identify non-overlapping pairwise sequences that are successfully mapped following performing the first and second mapping operations; and, a data terminal for displaying the results of the mapping operations generated by the data analysis unit to a user.

In still other embodiments, a computer-readable medium readable to execute a method of nucleic acid sequence analysis is taught. The computer-readable medium capable of executing the method comprising: receiving nucleic acid sequence information comprising one or more mate pair sequences, wherein mate pair sequences comprise non-overlapping pairwise sequences separated by an intervening sequence length; receiving nucleic acid sequence information comprising at least one reference sequence; performing a mapping operation for each of the one or more mate pair sequences in which the non-overlapping pairwise sequences are aligned to the at least one reference sequence by the steps of: performing a first mapping operation aligning the non-overlapping pairwise sequences to the at least one reference sequence with a selected mismatch constraint identifying non-overlapping pairwise sequences for which one of the non-overlapping pairwise sequences align to the at least one reference sequence while satisfying the selected mismatch constraint; performing a second mapping operation designating a window region of the reference sequence to align the non aligned pairwise sequence with a selected mismatch constraint; identifying non-overlapping pairwise sequences that are successfully mapped following performing the first and second mapping operations; and, outputting the results of the mapping operations.

DRAWINGS

The skilled artisan will understand that the drawings, described below, are for illustration purposes only. These figures are not intended to limit the scope of the present teachings in any way.

FIG. 1: illustrates an exemplary double stranded DNA fragment and associated mate pair primers (F3) and (R3) according to the present teachings.

Figure 2A:
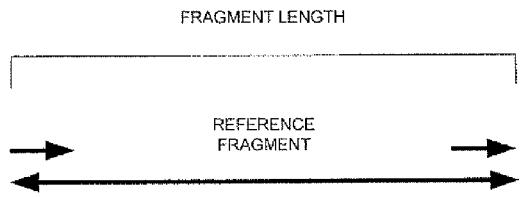
Figure 2A:
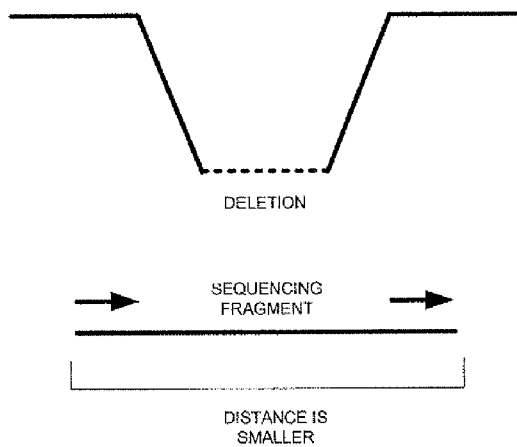

FIGS. 2A & B: illustrate the occurrence and relative size of insertions and deletions in a comparison between a reference fragment and a sequencing fragment according to the present teachings.

Figure 3A:
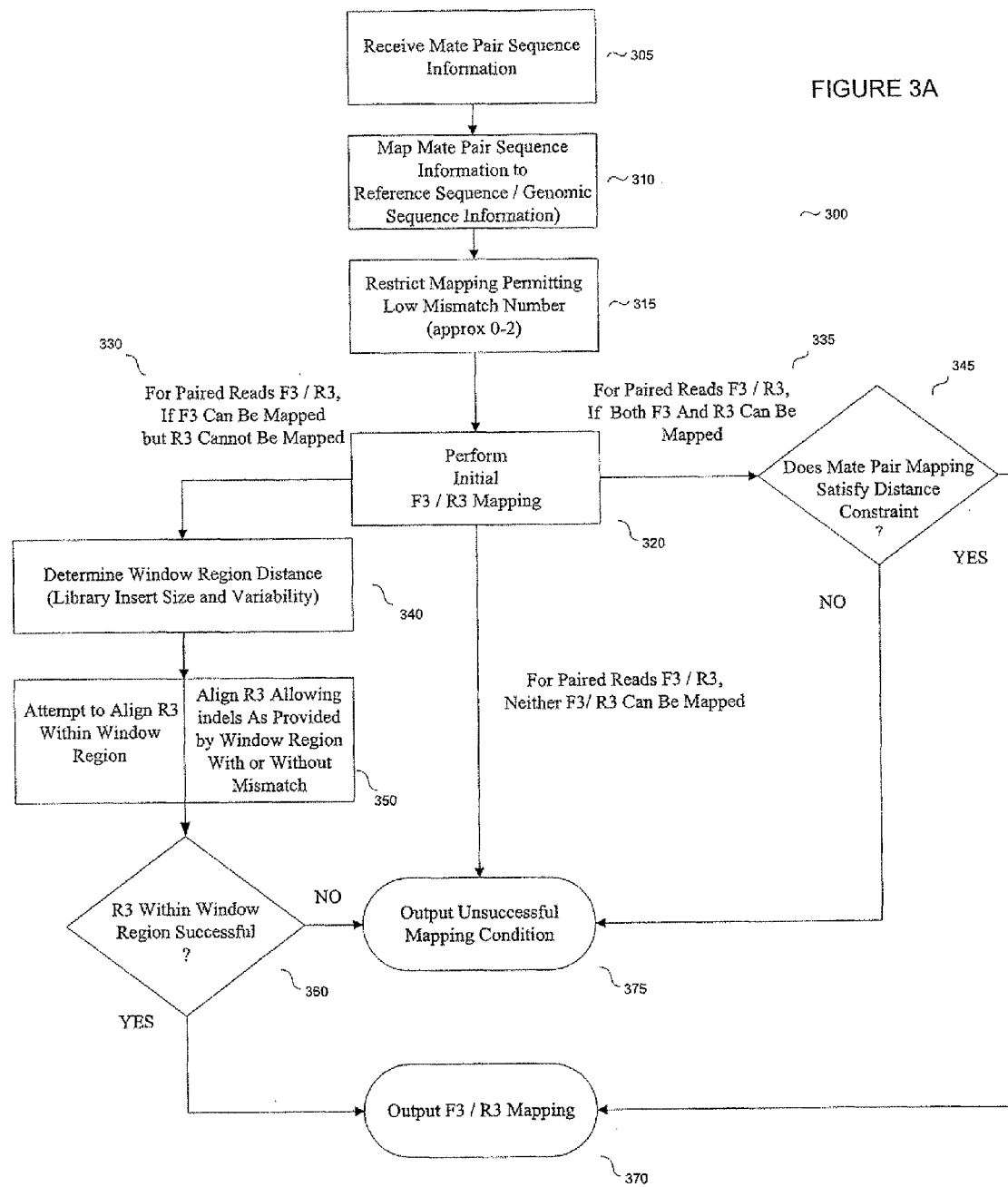

FIGS. 3A & B: illustrate flowcharts for mate pair sequence analysis according to the present teachings.

Figure 4:
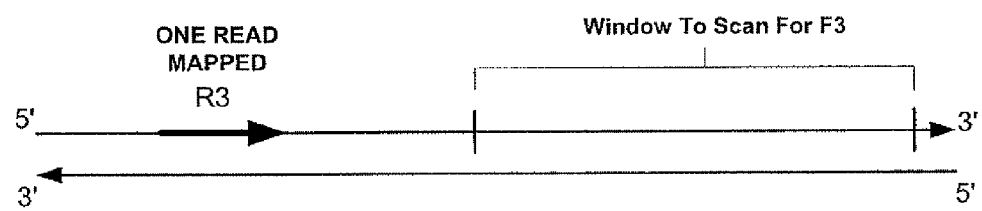
Figure 4:
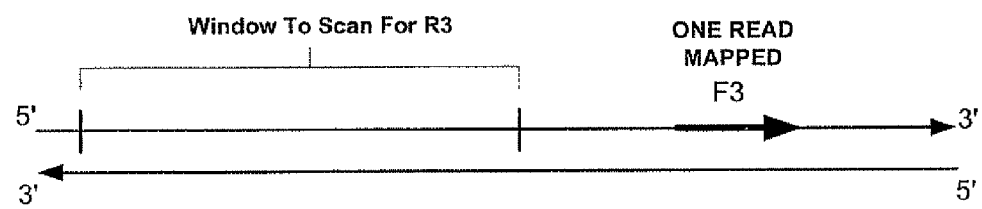

FIG. 4: illustrates the application of a search region/window scanning technique for use with mate pair sequence analysis according to the present teachings.

Figure 5:
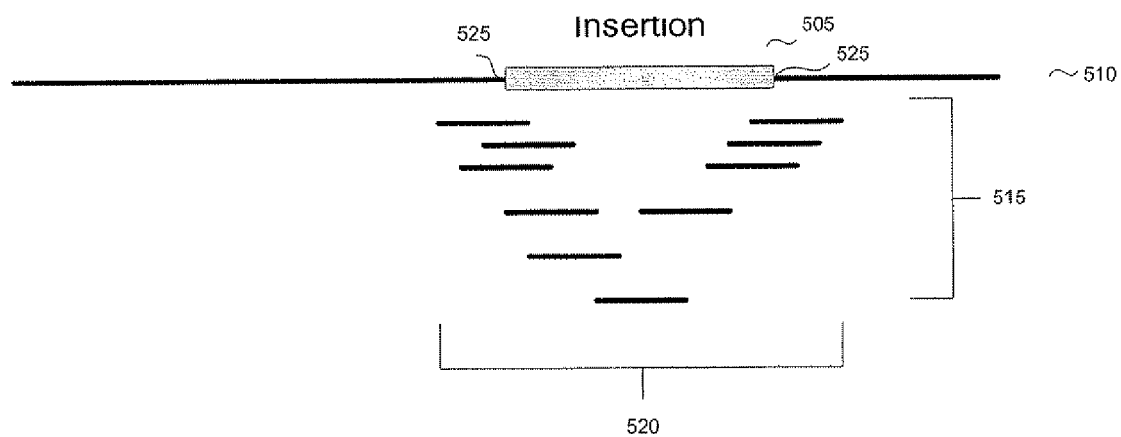

FIG. 5: illustrates a large insert identification approach according to the present teachings.

FIG. 6: illustrates exemplary validation and simulation results for mate pair analysis according to the present teachings.

Figure 7:
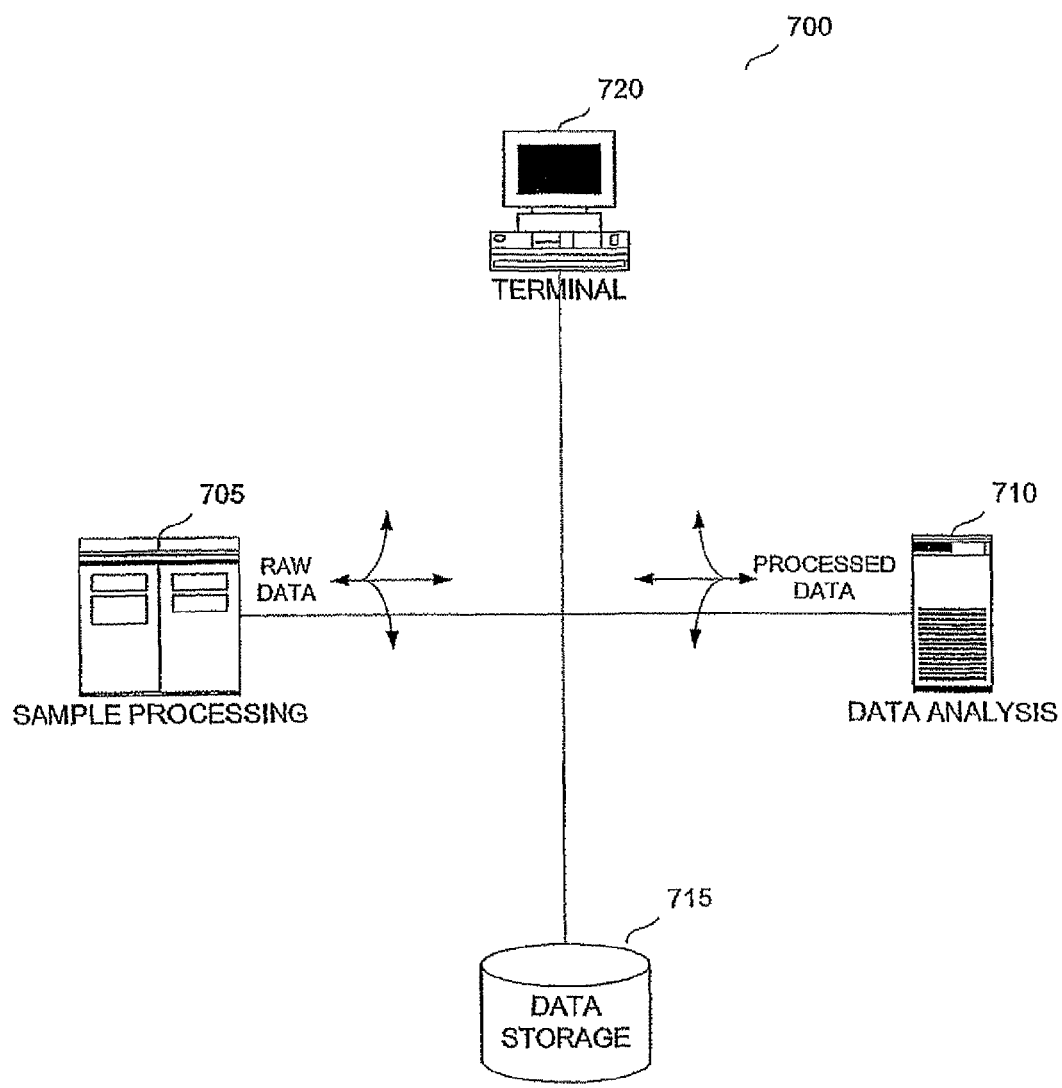

FIG. 7: illustrates an exemplary system for performing nucleic acid sequence analysis according to the present teachings.

DESCRIPTION OF EXEMPLARY EMBODIMENTS

It is to be understood that both the foregoing general description and the following detailed description are exemplary and explanatory only and are not intended to limit the scope of the current teachings. In this application, the use of the singular includes the plural unless specifically stated otherwise. For example, "a forward primer" means that more than one forward primer can be present; for example, one or more copies of a particular forward primer species, as well as one or more different forward primer species. Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "x" or "Y" or "X and Y".

The section headings used herein are for organizational purposes only and are not to be construed as limiting the described subject matter in any way. All literature and similar materials cited in this application, including patents, patent applications, articles, books, and treatises are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

In various embodiments, nucleic acid sequence information that may be adapted for use with the present teachings comprises mate-pair sequence information FIG. 1 illustrates an exemplary double stranded DNA fragment 50 and associated mate pair primers (F3)100, (R3)102. In a typical analytical paradigm, sequence information may be obtained by sequencing from both directions 120, 125 (e.g. 3' and 5' portions) of a nucleic acid fragment. For example, as shown in the illustration, primer pairs F3 and R3 span a portion of the nucleic acid fragment 50 with an intervening distance 105 of a known or approximated size 150. Such pair-wise sequence information, referred to as mate-pair information, generally constrains the placement and size of the sequencing reads within a sequence to be assembled 140. As used herein, the term "mate pair" may include fragment information for both ends of an insert in combination with the insert's size 150, such that the distance or sequence length separation between the two sequenced fragments is known to at least a first approximation.

In one aspect, short read mate-pair sequence information may be obtained by sequencing a portion of the nucleic acid fragment 50 using primer pairs F3/R3 such that sequence information is obtained correspond to a forward locality (3') 100 and distal locality (5') 102 with an intervening region 105. Typically, the sequence of the intervening region 105 is not provided for by the sequence information corresponding to the forward locality (3') 100 and distal locality (5') 102, however, the size or number of bases spanning the intervening region 105 may be approximately or accurately known (e.g. the sequence information obtained using the F3/R3 primer pairs does not overlap with respect to the reference sequence but rather is separated by the intervening sequence). As previously discussed, short read sequence information is typically significantly shorter in comparison to other sequencing methodologies such as Sanger sequencing based approaches. In one aspect, short read sequence information comprises sequence information from each primer F3/R3 having a size from between approximately 10-30 base pairs. In another aspect, short read sequence information comprises sequence information from each primer F3/R3 having a size from between approximately 25-50 base pairs. In another aspect, short read sequence information comprises sequence information from each primer F3/R3 having a size from between approximately 40-75 base pairs. It will be appreciated however that the application of the present teachings may be suitable for use with other sequence lengths and that sequence lengths arising from F3/R3 need not be identical to one another.

For mate pair reads the distance 105 between primers F3/R3 may vary from one primer pair to the next. In accordance with the present teachings, paired short read sequence information is generally separated by a distance 105 of approximately a few kilobases (Kb). For example, the distance between primers F3 100/R3 102 may reside between approximately 2-3 Kb, between approximately 4-7 Kb, or between approximately 8-15 Kb. It will be appreciated however that the application of the present teachings may be suitable for use with other mate pairs reads with distances between primers F3 100/R3 102 greater or less than those listed above.

Methodologies for generating mate pair sequence information in accordance with the above-indicated sizes are known in the art. For example, United States Patent Application Publication number 2006/0024681 entitled "Methods For Producing A Paired Tag From A Nucleic Acid Sequence And Methods Of Use Thereof" describes various approaches for developing nucleic acid libraries suitable for use with mate pair sequencing approaches the contents of which are hereby incorporated by reference in their entirety. In contrast, U.S. Pat. No. 6,714,874 entitled "Method and System For The Assembly Of A Whole Genome Using A Shot-Gun Data Set" describes methods and systems for assembling a genome from a shot-gun set of end sequenced DNA fragments using larger DNA fragments and sequencing information as compared to short read sequence information, the contents of which are hereby incorporated by reference in their entirety. Previous work relating to software tools for analyzing mate pairs assemblies in the context of larger nucleic acid fragments and whole genome shotgun assemblies include "A Tool For Analyzing Mate Pairs In Assemblies (TAMPA)", Dew et al., Journal of Computational Biology, Vol 12, No. 5, 2005 and in the context of shorter nucleic acid fragments include "An Analysis Of The Feasibility Of Short Read Sequencing", Whiteford et al. Nucleic Acids Research, Vol 33, No. 19, 2005 and "Fragment Assembly With Short Reads", Chaisson et al., Bioinformatics Vol 20, No. 13, 2004 the contents of which are incorporated by reference in their entirety. In view of these articles, it is observed that potential problems and pitfalls exist when applying conventional sequence assembly techniques to short read sequence data.

Figure 2B:
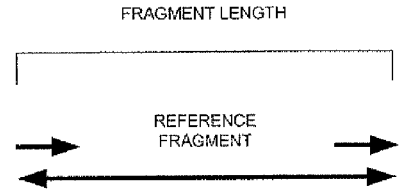
Figure 2B:
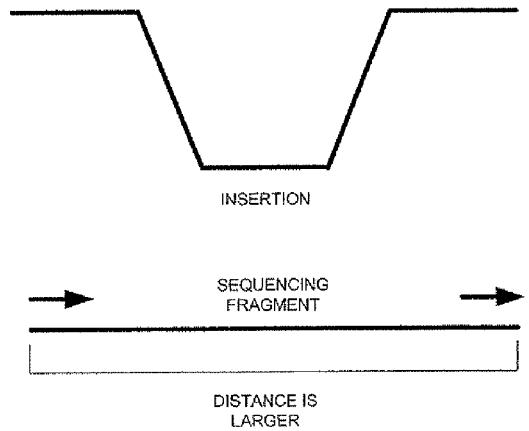

As shown in FIGS. 2A and 2B mate pair sequencing applications according to the present teachings can be used to detect or identify insertions and deletions of varying indel sizes. For relatively large size indels, one approach to indel identification can be determined as the deviation from the average distance which can be used to derive the existence and size of an indel. For the purposes of the present teachings the size of large indels is considered to include those sized approximately 0.2 Kb and greater. In various embodiments, a further advantage of the present teachings is that the disclosed methods can be used to identify deletions, including those with sizes of up to approximately 1 Kb, as well as insertions As will be described in greater detail hereinbelow a mini-assembly approach may be used in the detection/identification process.

According to the approach described above, larger indels can be generally identified by this methodology. Small to medium size indels, however, present a more challenging problem when using mate pair sequence information and thus other potentially more efficient alternatives are discussed. For the purposes of the present teachings the size of medium indels is considered to reside between approximately 10 bp and 200 bp for deletion, and 5 bp and 200 bp for insertion. Likewise, for the purposes of the present teachings the size of small indels is considered to reside between approximately 1 bp and 10 bp for deletions and 1 bp and 5 bp for insertions.

In various embodiments, small to medium size indels may be identified using mate pair sequencing reads and alignments directly. The approach taken however, places certain constraints on the alignment process so as to reduce the computational complexity of the analysis. The size and number of short read sequence data is such that unconstrained alignments of short reads to reference sequences that allow for gaps for insertions and/or deletions create intractable and time consuming problems. Furthermore, an unconstrained mapping typically leads to numerous potential false alignments and reduces the overall quality and confidence in the analysis. The approach of the present teachings overcomes this obstacle imposing certain constraints on the mapping/alignments so as to improve the result quality while reducing the computational complexity of the process. In the instance of paired read information as provided by the mate pair sequence information where the approximate distance between the tags/primers is know, it is increasingly likely that at least one of the two reads in the pair will not overlap with an indel and consequently such a characteristic may be advantageously utilized to reduce or limit the number of false alignments.

The flow diagram 300 depicted in FIG. 3 illustrates a stepwise analysis approach that may be used to identify small and medium size indels in accordance with the present teachings. Commencing in state 305 mate pair sequence information (e.g. tags) including reference sequence information is received or collected and prepared for further analysis. Such mate pair sequence information may comprise, for example, base sequences associated with one or more mate pair primer sets (e.g. F3/R3 primers as shown in previous illustrations). The base sequence information may also include additional information including for example quality or confidence values, reference sequence locality information, annotations indicating the exact or approximate distance between the mate pair primers, and other information. Reference sequence information may comprise various types of base sequences for example for one or more target genomes or samples of interest. It will be appreciated by one of skill in the art that the type of mate pair and reference sequence information used in the analysis may be obtained in numerous manners. For example such information may be transmitted directly from a sequencing instrument platform or retrieved from a database used for storing such information. The mode and manner of collecting, transmitting, retrieving, processing, and/or preparing sequencing data for use with the analysis approaches of the present teachings is not to be construed as limiting to the scope of the present teachings.

Once appropriate sequence information has been collected in state 305 a mapping/aligning operation is performed in state 310. The mapping operations performed herein are generally shown in previous illustrations and are used to determine the appropriate positioning of the mate pairs with respect to the reference sequencers). It will be appreciated that such mapping operations can be conducted in a substantially automated manner without user interaction or alternatively various graphical user presentations of the mapping may be programmatically implemented.

The mapping operations continue in state 315 where the mate pair analysis determines the positioning of the mate pairs with respect to the reference genome allowing for a selected number or range of mismatches between each mate pair sequence (e.g. F3/R3). As one exemplary range of mismatch tolerances, between 0-2 mismatches may be permitted for a short read mate pair sequence. Such a mismatch tolerance is sufficiently stringent to aid in accurate identification of the appropriate placement of each mate pair with respect to the reference sequence. Furthermore, providing a permissible mismatch number or range allows for a degree of error tolerance in the sequence information and/or the alignments to facilitate determination of the most likely positioning of the mate pairs with respect to the reference sequence. As will be described in greater detail hereinbelow, it is possible that either none, one, or both mate pairs may align with the reference sequence.

In performing the initial mapping in state 320, a determination is made as to whether either F3 and/or R3 can be mapped to the reference sequence given the permissible mismatch tolerances described above. As shown by outcome 330, in the instance that a single mate pair can be mapped to the reference sequence (e.g. F3 can be mapped but R3 cannot) a window region distance determination is made in state 340. The window region distance denotes a range of bases that deviate from the approximate or expected distance between the mate pair primers but which may account for the presence of additional bases resulting from one or more insertions or the absence of expected bases between the mate pairs resulting from a deletion.

An exemplary window region distance and associated mate pair scanning and alignment approach is shown in FIG. 4. In one exemplary instance, a mate pair sequence (R3 in the upper portion of the diagram and F3 in the lower portion of the diagram) is successfully mapped to the reference sequences given the previously described mismatch tolerances. Based on the size of each mate pair and the approximate or expected distance between the mate pairs, a window of a selected base sequence number or range is identified for which to attempt to align the corresponding mate pair sequence to (F3 in the upper portion of the diagram and R3 in the lower portion of the diagram). It is within this region that the method referred to in FIG. 3 attempts to map the corresponding mate pair. It will be appreciated by one of skill in the art that such an approach allows for a degree of flexibility in mapping to account for insertions and/or deletions with respect to the reference sequence which might otherwise prevent alignment of the mate pair sequences with the approximated or expected intervening sequence length.

Referring again to FIG. 3, in state 350 the mate pair tag (e.g. R3 in FIG. 3A state 350) which could not readily be mapped to the reference sequence is aligned within the window region. During this process, the alignment of the mate pair tag accommodates alignment with and/or without mismatches of a specified number or amount in the sequence information. In one aspect, such an approach provided for an "anchor" in the mapped mate pair tag (e.g. F3) and permits a sliding or flexible mapping of the unmapped mate pair tag (e.g. R3).

In state 360, if a successful mapping of the previously unmapped mate pair tag (e.g. R3) is accomplished, the mapping of both mate pair tags and associated sequence information may be identified and outputted in state 370. If the previously unmapped mate pair tag (e.g. R3) could not be mapped within the window region according to the previous step, then the lack of mapping may be identified and output in state 375.

Reverting again to the initial mapping performed in state 320, determining whether either F3 and/or R3 can be mapped to the reference sequence. As shown by outcome 335, in the instance that both mate pair tags can be mapped to the reference sequence (e.g. both F3 and R3 can be mapped) a distance constraint determination is made in state 345. Verifying that the distance between the mate pairs matches the expected or approximated distance between the mate pair tags significantly reduces the likelihood of false mappings. Such a determination also desirably avoids false positive conditions which would otherwise occur with greater frequencies relative to longer conventional sequencing reads such as those provided by Sanger sequencing applications. Thus in state 370, if both mate pair tags (F3 and R3) are successfully mapped and distance constraints between the two are met the sequence information and results may be identified and output as described above. Likewise, for mate pair tags which fail to satisfy the distance constraint conditions, the results may be output in state 375 as discussed previously.

Figure 3B:
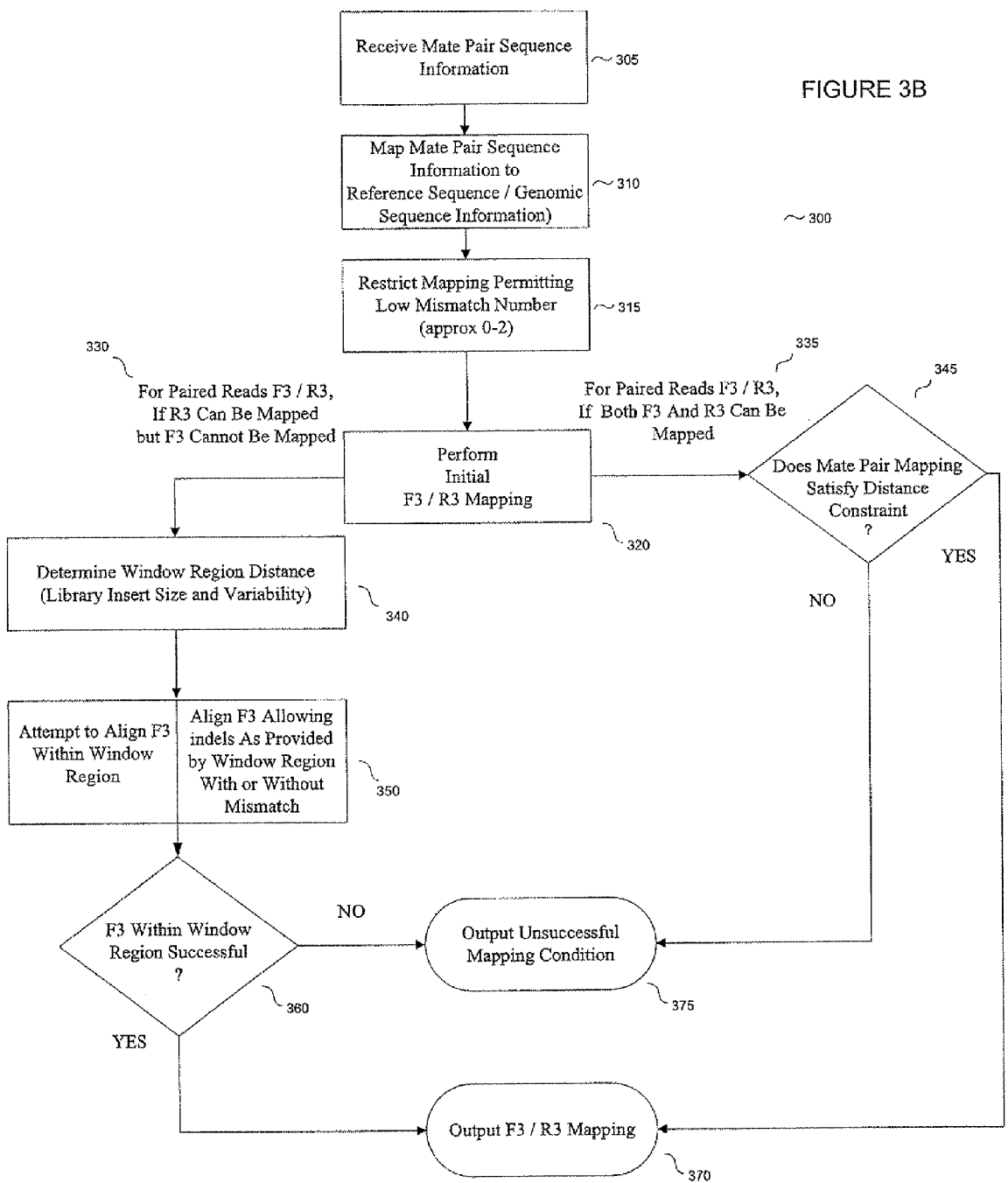

FIG. 3B provided an analogous analytical approach for mate pair sequence analysis wherein the mate pair tag which is successfully mapped in state 370 is the opposing mate pair tag (e.g. R3 is mapped as compared to F3). Those of skill in the art will appreciate that the implementation of the analytical approach would proceed in a similar fashion with expected outcomes as indicated in the Figure. Furthermore, it will be appreciated that these analytical approaches may be readily implemented and/or coded using various software packages and/or programming languages and as such all such implementations are conceived to be within the scope of the present teachings.

In various embodiments, the above-described analytical approach for indel identification can be summarized into two principle stages. In the first stage the mate pair tags or reads may be aligned allowing for a small number of mismatches and in the second stage, for pairs of mate pair tags or reads in which only one mate pair tag is successfully mapped, an attempt may be made to align the non matching second mate pair tag to allow a permissible gap in the read but still constrain the alignment to the relatively small region. The location of the region may be considered as relative to the location of the first tag that mapped to the reference sequence and may be determined by the size of the clones in the library.

FIG. 5 illustrates an approach to determining an insertion using a mini-assembly approach. This approach may be readily utilized when attempting to identify a relatively long insertion 505 (rather than a duplication of another region) that may be present in a genome or sequence of interest 510. In the illustration, the insertion 505 in the exemplary sequence 510 is shown as the thickened line. Reads are indicated by shorter lines 515 under the exemplary sequence 510. It is possible to assemble the reads to cover 520 the insertion 505. In this example, at the junction 525 of the insertion either the first half or the second half of the reads 515 match the reference sequence 510.

Using this approach to assembly, a rule that there exist a perfect match for at least N bases of the overlapping region between reads may be enforced. For those reads matching this conditions, the shortest path in the overlapping group of reads may be traversed to identify the insertion.

FIG. 6 illustrates two tables of statistical results for the above-described sequence analysis approaches. The results presented in Table 1 provide observed false positive rates when detecting deletions and insertions according to the mate pair analysis approach of FIG. 3. To derive these numbers approximately 1 million paired reads from the *C. elegans* genome where used adding 10% uniform random sequencing errors to the read with a read length of approximately 25 bp. For this experiment, 2 mismatches where allowed in accordance with step 315 and M mismatches allowed with at least 8 bp on either side of the indel in accordance with step 350 in FIGS. 3 A/B.

The mapping and indel finding approach described herein was then applied to this set of reads and subsequently the number of identified indels was counted. False positive rates correspond to the portion of pairs that find an indel using the approach described in FIG. 3. False positives for deletions are shown in Table 1 and insertions shown in Table 2. It will be appreciated that since the reads are sampled from the reference sequence without any indels, this simulation estimates the false positive rate. For results shown in Table 1, the number of deletions is presented in column 1A and it can be observed that when the reads are aligned without mismatch, deletions of up to approximately 100 bp can be found with a substantially low false positive rate. Where D is the maximum size of deletion allowed in the approach set for in FIG. 3. Similarly, the results for insertions is shown in Table 2 are even better than that for deletions presented in Table 1. Where I is the maximum size of an insertion allowed in the approach set for in FIG. 3. Thus, using only the alignment of reads, insertions of up to approximately 8 bp can be readily identified.

One significant aspect of the present teachings is that by their application, one may advantageously align pairwise short read sequence information with a greater degree of confidence and accuracy as compared to conventional approaches. For example, in the case where one of the two mate pair sequences does not readily align to the reference sequence as a result of the presence of an indel within the intervening sequence the window scanning approach may be used to "rescue" the non-aligned mate pair sequence and determine an appropriate positioning of this sequence with respect to the reference sequence. It will be appreciated that applying these techniques thus improves utilization of the mate pair sequence information and avoids undesirable "loss" of non-aligned mate pairs that result from the presence of indels.

Likewise, the miniassembly approach demonstrated by the present teachings provides an efficient manner in which to "span" an insertion thereby permitting suitable alignment of the mate pair sequences while identifying the presence of the insertion with respect to the reference sequence.

FIG. 7 illustrates an exemplary system 700 which may be used to perform sequence analysis and indel detection according to the aforementioned methods. In one aspect, a sample processing component 705 may provide means for performing operations associated with sample processing and data acquisition. These operations may include by way of example; labeling, amplifying, and/or reacting the sample in the presence of a suitable marker or label, exposing the sample to an appropriate analysis substrate or medium; and detecting signals or emissions from the sample which will serve as input data for the sequence analysis and indel detection methods. Instruments which may be associated with these operations include but are not limited to array-analysis instruments, sequencing instruments, fluorescent signal detection instruments, thermalcyclers, and other such instruments used in sample processing and data acquisition.

Raw data provided by the sample processing component 705 may be subsequently stored in a data storage component 715. This component 715 may comprise any of various types of devices designed for storing of data and information including for example; hard disk drives, tape drives, optical storage media, random access memory, read-only memory, programmable flash memory devices and other computers or electronic components. Furthermore, the data and information obtained from the sample processing component 705 may be stored and organized in a database, spreadsheet, or other suitable data structure, data storage object, or application which operates in connection with the data storage component 715.

In various embodiments, a data analysis component 710 may be present within the system 700. This component 710 possesses functionality for acquiring data and information from the sample processing component 705 or the data storage component 715. The data analysis component 710 may further provide a hardware or software implementation of the aforementioned sequence analysis and indel detection methods. In one aspect, the data analysis component 710 is configured to receive input data and may return processed data including sequence analysis and indel detection information which may be stored in the data storage component 715 or displayed directly to the investigator via a display terminal 720.

Each of the functionalities of the aforementioned components 705, 710, 715, 720 may be integrated into a singular hardware device or into one or more discrete devices. These devices may further possess network connectivity facilitating communications and data transfer between the devices as desired by the investigator. It will be appreciated that numerous suitable hardware and software configurations may be developed which implement the sequence analysis and indel detection methods of the present teachings, as such each of these configurations should be considered but other embodiments of the present teachings.

Exemplary Analysis and Statistical Treatment

According to the analytical approach of the present teachings the method for finding indels may comprise initially mapping reads requiring substantially high similarity (allowing for a relatively high degree of stringency such as either a perfect match or 1 mismatch). Thereafter, each pair of reads in which only one tag maps uniquely or with a high degree of confidence the other corresponding tag is aligned to accommodate indels and/or more mismatches in the region that is substantially the correct distance away from the mapped tag. In various embodiments, this distance is determined by the library insert size and its variation.

In evaluating the above-described methods the probability that a random sequence can achieve the same alignment may be considered in a manner similar to the statistical significance analysis of local alignment. In one aspect, using an independent random sequence model, relatively low false positive rate may be observed (alignment from random sequence) such that approximately 3 mismatches and one deletion of up to 30 bps may be accommodated. For insertions, a 10 bp insertion may be readily identified when allowing no mismatch.

This analysis suggests that alignment is not random. Upon further consideration, for an alignment with a deletion, for example, there could be two possible hypothesis, one is that the deletion is real, the other is that the read is the result of sequencing errors.

Testing these hypotheses the probabilities the read supports either hypotheses may be evaluated from the probability of observing the read under the two hypotheses (one with an indel, the other without), and then decide when to accept the indel. The analysis suggests that indels that reside in the middle of the read are of high confidence.

Combining these analyses with other results, for a given genome size, a certain coverage rate, a read length, and a sequencing error rate, the chance of finding an indel can be estimated. For example, the chance of finding a deletion of up to 30 bp with sufficient confidence is $1-(1-P)^{(kL)}$, where k is sequencing coverage, $P=xy(R-10)/L$, where x is the probability that a read has at most 3 sequencing errors, y is the probability the paired read has at most 1 mismatch, R is the read length and L is the genome length.

It will be appreciated that the problem of aligning short reads to a reference sequence while allowing gaps for insertions and/or deletions by conventional means leads to an unacceptably time consuming process and may lead to numerous false alignments. According to the present teachings, by using paired reads where the approximate distance between the two tags are known, it can be determined that at least one of the two reads in the pair will not overlap an indel and this consequently will limit the false alignments.

According to the present teachings, indel detection/identification can proceed using reads that are aligned allowing for a small number of mismatches and for pairs of reads in which only one tag mapped, attempting to align the non matching second tag allowing a gap in the read while constraining the alignment to the relatively small region R. The location of R is relative to the location of the first tag that mapped to the reference sequence and may be determined by the size of the clones in the library. The size of R may be indicated by |R| and if there is no confusion P may be used in place of |R|. Note that the size of R may be determined by the range of the insert size rather than by the insert size itself.

Bayesian Approach and Relation to False Discovery Rate

One manner in which to assess whether the alignments found above represent real indels is to assess how likely it is that two random sequences can form such an alignment. Such an approach is similar to the statistical significance estimate that may be conducted for local sequence alignment. However, such a measure does not take into account the likelihood of the existence of an indel. Even if random sequences have a low chance of forming an alignment, it does not necessarily indicate that the indel is real and thus there could be other explanations such as sequencing errors.

Applying a Bayesian approach to estimate the confidence that an alignment is real may be useful to test the utility of such an analytical approach to sequence analysis. When a read (or reads in context of a mini-assembly as will be described in greater detail herein below) aligns to an indel, there are two potential scenarios: (1) there is a real indel at this position of the reference sequence; and the reads in the alignment arise from this indel region (H1); (2) there is no indel at this position, and the reads in the alignment arise from another region and form the observed alignment due to sequencing errors (H0). Estimating P(H0|reads) and P(H1|reads) where "reads" is the set of reads that align to the indel P(H1|reads)/P(H0|reads) may be used as a measure of confidence that the reads find a real indel. In one exemplary manner, when the measure is larger than 10, H1 may be accepted, e.g. that the indel is real. Restated another way this enforces that for every 11 (10+1) indels that are determined to be real, approximately only 1 will be false.

Using a Bayes' theorem approach, P(H1|reads)=P(reads|H1)P(H1)/P(reads) and P(H0|reads)=P(reads|H0)P(H0)/P(reads). As discussed above, the ratio P(H1|reads)/P(H0|reads) is of interest, which is P(reads|H1)P(H1)/P(reads|H0)/P(H0). In practice, indels are relatively rare, P(H1) is typically much smaller than P(H0) and only the ratio P(H1)/P(H0) is important. For simplicity, set P(H0)=1 and therefore, P(H1|reads)/P(H0|reads)=P(reads|H1)P(H1)/P(reads|H0). In the following analysis the three above terms are estimated and evaluated.

The following assumptions and lemmas may be used in the statistical analysis.

Assumption 1 The reference sequence follows a generally uniform independent random distribution, e.g. each base of the sequence is independently distributed with A, C, G and T each having a probability of approximately ¼.

Assumption 2 Sequencing errors are generally uniformly distributed with an error rate of p per base; and generally only cause mismatches.

Note other more general sequencing error models can readily be used with the presented results adapted thereto.

Assumption 3 (Uniform shotgun sampling) Each read r is generally equally likely to be sampled from any position of the reference sequence. For paired reads, the region where one read is from is known, the read may be assumed to be sampled uniformly in that region.

It will be appreciated that this assumption may be used for simplicity of discussion and other known biases can be readily incorporated.

Lemma 1 Let r be a read and R a sequence. The chance that r is a read from sequence R is: $P(r|R)=\Sigma_j P(r|R_j)P(R_j)$, where $R_j$ is the event that read r is sampled from R starting at position j.

Lemma 2 Let r be a read and R a sequence. If |R|=|r| and r and R have x mismatches and y matches when aligned to each other, it can be estimated that $P(r|R)=p^x(1-p)^y$.

Lemma 3 Let r be a read and R a sequence, then $E(P(r|R))=(1/4+p/2)^{|r|}$.

Proof. From Lemma 1, $E(P(r|R))=E(\Sigma_j P(r|R_j)P(R_j))=|R|E(P(r|R_j)P(R_j))=E(P(r|R_j))$ since $P(R_j)=1/|R|$, and each $P(r|R_j)$ is generally identically distributed.

From lemma 2, $$E(P(r|R_i)) = \sum_j \binom{|r|}{j}\left(\frac{1}{4}\right)^j\left(\frac{3}{4}\right)^{|r|-j} p^{|r|-j}(1-p)^j$$

$$= \left(\frac{1}{4}(1-p)+\frac{3p}{4}\right)^{|r|}$$

$$= \left(\frac{1}{4}+\frac{p}{2}\right)^{|r|}.$$

Noting the following useful observations.

Observation 1, from Lemmas 1 and 2, P(reads|H0) can be estimated by aligning r to each position of a region that is the correct distance and orientation from the location anchored by the corresponding tag. When this is time consuming, it can be estimated by only finding significant alignments (with fewer mismatches), and use Lemma 2 on those alignments, and for all the other positions, use the expected probability from Lemma 3.

Observation 2, one aspect of the analysis below may be to determine the type of alignment that is used to confidently predict an indel. It is desirable to determine the requirement for the alignments such that when H1 is true, the reads that are found are likely to have a high value for P(H1|reads)/P(H0/reads). In this instance P(reads|H1) may be estimated since the reads are aligned to the indels. However, P(reads|H0) is harder to estimate since there is usually no known alignments for those reads to the reference sequence. However, the average analysis may be used to estimate P(reads|H0) and obtain the necessary requirement for the alignments (e.g. size of indel, number of mismatches, size of overlap etc) in order to accept it as a potential indel. To identify an indel, observation 1 may be used to estimate P(reads|H0) for each individual case.

Finding Deletions

Evaluating what type of alignment can lead to a confident prediction of the existence of a deletion one can focus on an alignment with exactly one deletion. Two parameters can be used describe the alignment: the size of the deletion D and the number of bases X in the shorter of the two sequences flanking the deletion. Evaluating what constraints on D and X are satisfied in order to confidently predict a deletion as well as determining the typical size of a deletion to be found can be helpful.

In one exemplary case, where P(r|H0) is relatively large and accepting this as a deletion may lead to false positive identification. Using a prior $P(H1)=10^{-4}$ D(S), meaning there is approximately 1 deletion every 10000 bases and the distribution of length is given by D(S). It is becomes increasingly difficult to estimate D(S) and thus for simplicity $D(S)=2^{-S}$, the geometric distribution may be used.

Consequently:

$P(H1|read)/P(H0|read)=10^{-4}2^{-S}P(read|H1)/P(read|H0)$

From Lemma 2, $P(read|H1) \leq p^m(1-p)^{L-m}/R$ where L is the read length and m is the number of mismatches in the deletion alignment. For $P(read|H0)$, if the shorter flanking sequence has n mismatches, then estimate $P(read|H0)=p^n(1-p)^{L-n}/R$, assuming more mismatches on the other flanking sequence.

For the typical case, on average, there are approximately 3X/4 mismatches and half of the m mismatches are in the second half of the flanking sequence. In this typical case, from Lemmas 2 and 3, $P(read|H0)=p^{\wedge}(3X/4+m/2)(1-p)^{\wedge}(L-3X/4-m/2)/R+f$, where $f=(0.25+p/2)^L$.

Since f is generally negligible compared to the other term.

$$P(H1|read)/P(H0|read) = p^{\frac{m}{2}-\frac{3X}{4}}(1-p)^{\frac{3X}{4}-\frac{m}{2}}10^{-4}2^{-S} \quad (1)$$

For m=2 and L=25, p=0.05 (real sequencing error rates may be even smaller), solving $P(H1|read)/P(H0|read)>10$ using the average formula for $P(H0|read)$, yields X>10 when S=10. This suggests that to a deletion of up to 10 bases one can be placed when the deletion is in the approximate middle 5 bases of a read. One practical approach is to first find the deletion alignment, check the two flanking sequences to get the value n for the formula $P(H1|read)/P(H0|read)$ and then directly check whether the ratio is larger than 10. Also it may be noted that when there is more than one alignment in the region, a hypothesis can be formed for each alignment and thereafter check $P(H|read)$ for each hypothesis.

The above discussion suggests that a single deletion alignment is enough to confidently find a deletion in the range of approximately 10 bases. When multiple reads match the same deletion, one may confidently find longer reads. With the same 0.05 error rate and L=25, if two reads align to the same deletion in the middle 5 bases then a deletion up to nearly 40 bases may be readily found. It will be appreciated that high-throughput sequencing platforms such as the Applied Biosystems SOLiD instrument may generate approximately 50 to 100× coverage, and one may expect 10 or more reads to cover the deletion locality thus providing the opportunity to find larger deletions of 300 bps or longer.

Estimating the probability that each deletion can be found using the deletion alignment and detecting criteria above a single read with at most 2 sequencing errors to cover the junction with the middle 5 bases of the read is sufficient. Letting G be the genome length and supposing have KG total good pairs of reads of 25 bps (base coverage of 50KX). In one aspect, a good pair suggests that both reads have at most 2 sequencing errors. For any deletion, the chance of finding one read that covers it in the middle 5 bases is $1-(1-5/G)^{2KG} \approx 1-e^{-10K}$ when G is large.

For K=1, 0.5 and 0.25 and large G, the chances of finding a deletion are 99.995%, 99.32% and 91.79%, respectively. The number of raw reads may be estimated and is useful to achieve this number of good pairs. At K=0.25 level, approximately 12.5× base coverage of good pairs would suffice. It may also be noted that when a deletion is not placed in the middle 5 bp of a read, one may still confidently identify it if there are multiple reads covering it near the bordering regions.

Finding Insertions

Finding Insertions with Alignment Alone

In various embodiments, an analysis of insertion alignments can be performed that is similar to that for deletion alignments except that a read that includes an insertion can only have part of it mapped to the reference sequence giving rise to a higher rate of false positives.

Where an insertion alignment occurs, two hypotheses H0 and H1 may be formed as done previously. To estimate P(H1), it can be estimated that at each position, there is $10^{-4}$ chance of having an insertion and there is a geometric distribution for the length of the insertion. For an insertion of length S, each of the $4^S$ sequences of length S is generally equally likely to be inserted.

Accordingly $P(H1)=10^{-4}8^{-S}$

Therefore $P(read|H1)=p^m(1-p)^{L-m}/R$

Defining f as the expected probability of observing a read in the region of R bases, and from Lemma 2, gives $f=(0.25+p/2)^L$. Using the average number of mismatches as before, therefore $P(read|H0)=\max(f,p^{3L/4-3X/4+m/2}(1-p)^{3X/4-m/2+L/4}/R)$, where X is the length of the longer of the two flanking regions surrounding the insertion.

From above, $P(H1|read)/P(H0|read)<p^m(1-p)^{L-m}P(H1)/(fR)$.

If m=1, L=25, R=3000, and p=0.1, $P(read|H1)/P(read|H0)<3.14\times10^3 8^{-S}$ and it is less than 10 when S>2.76. Therefore, at a sequencing error rate of 0.1, to confidently find an insertion, the length of the insertion should be at most 2. Lowering the error rate to 0.05, the above calculation leads to the conclusion that the size of the insertion should be smaller than 6 for confident detection is this example.

It is clear that, when p=0.1 and $X \geq 14$, $q(X):=p^{3L/3-3X/4+m/2}(1-P)^{3X/4-m/2+L/4}/R>f$. Solving $P(H1|read)/P(H0|read)>10$, $X \leq 14$ when S=2 and $X \leq 16$ when S=1, so the shorter flanking region should be at least 9 or 8 bases long, respectively. When p=0.05, a similar calculation leads to $q(X)>f$ when $X \leq 16$ and it can concluded that the shorter flanking region should be at least 6 bases long.

The above calculation demonstrates that finding an insertion using a single read may be difficult and generally short insertions can be found. In the next section multiple reads will be used to cover longer insertions.

Finding an Insertion Using a Mini-Assembly

For a typical case when a long novel insertion (rather than a duplication of another region) is present in a genome. Read A overlaps B, denoted O(A,B), if a suffix of A of at least h bps long is a prefix of B. A digraph G=(V,E) is as follows: V includes all reads, there is a direct edge from A to B if O(A,B). For each read A whose prefix of at least g bps long matches perfectly to the reference ending at position t, call node A a starting node at position t. For each read A whose suffix of at least g bps long matches perfectly with the reference starting at position t call node A an ending node at position t. An insertion after the position t in the reference is a path from a starting node at position t to an ending node at position t+1.

The model above uses perfect matches and makes the analysis below easier. More generally, an overlap can be defined as approximate matches. Also note that if a prefix of a read matches to positions a, a+1, ..., a+u of the reference genome, and u>g, it is possible that the insertion may start after positions a+g, a+g+1, ..., a+u, when the first bases of the insertion are the same as the bases immediately after the insertion. To address this issue, one can produce u−g+1 nodes for the read corresponding to starting the insertion at position a+g, ..., a+u. The ending positions are treated similarly.

The path described above corresponds to an insertion (to be later determined if real). One proposition is: For any insertion, determine the likelihood that sufficient reads are present cover it (i.e., find a path in G that covers the insertion).

Another proposition is: Given that a path in G can be found, determine how likely it is the result of random reads.

Before answering the two questions above, refine the above path finding approach can be useful. Using paired information and looking for insertions one region at a time may be helpful. Selecting a small region (for example, approximately 3 Kb) in the reference genome, and attempting to find insertion in this region using paired information, it is possible to find all reads that may potentially map to this region. After removing reads that map to the region with up to, for example, 6 mismatches (these reads can be explained by sequencing error), one can use the rest to form the graph G and find the path in it.

Once can also use coverage map to limit the search for insertions. Note that, at high sequencing coverage, the place of insertion usually shows a noted drop in coverage. One can limit the search to a very small region surrounding those low coverage regions.

Once a path in the graph is identified, the hypothesis may be tested that the path corresponds to a real insertion. Given a path with n nodes (reads) one may attempt to map other reads to the insertion derived from the path to get a consensus sequence for the insertion. This will increase the support for the hypothesis that the insertion is real.

Again using H1 and H0 and assuming h=g. If n reads are found by the approach described previously, $P(reads|H1) = (1-p)^{Ln}/R^n$. To estimate $P(reads|H0)$, the average analysis may be used as before. For n reads of 25 bases and a random sequence of size R, from Lemma 3, $P(reads|H0) = f^n$.

As in the last subsection, $P(H1) = 10^{-4} 8^{-S}$, where S is the length of the insertion. From the way the path is built, $S<(L-h)n-h$. When $p=0.1$, $R=3000$ and $h=16$, $fR=2.54\times 10^{-10}$ and $$\frac{P(H1|reads)}{P(H0|reads)} \geq \frac{10^{-4}(1-p)^{nL}}{(fR)^n 8^{(L-h)n-h}} \geq 2.8\times 10^{10} \times 2.1^n \gg 10.$$

Finding a path as above with h=16, one can be confident it is true. The calculation indicates that when the insertion is novel, regardless of its length, if the mini-assembly approach above can find a path to cover it, one can be very confident it is real.

The novel insertion requirement enables use of Lemma 3 to estimate $P(reads|H0)$. In practice, it can be estimated directly by mapping all the reads to the region allowing many mismatches. Then it can be calculated that $P(H1|reads)/P(H0|reads)$ and decide whether to accept the H1, so even if the inserted sequence is "somewhat" related to the neighboring region, the ratio may still be large enough to accept the insertion. When the path is found, a large part of the insertion may be covered by only three reads. A post-processing step may be performed by aligning other reads to this new inserted sequence allowing some number of mismatches. These will lead to a multiple alignment of reads and a standard base calling routine can be used to do the base-calling (similar to that of de novo sequencing).

In evaluating if there is an insertion, how likely is it that the mini-assembly routine can identify it one may assume to have an insertion of length S. It may be seen that for each position of the insertion, there is at least one read that is perfect (no sequencing error) that contains the position in its interior excluding the last 8 bps from both ends, then there is a path covering it. If the genome size is G, and there are KG perfect reads, then the chance that this happens is at least $q^S$, where $q=1-(1-1/G)^{KG}\approx 1-e^{9K}$.

When K=1, $q^{1000}=0.8838$ and $q^{500}=0.94$. When K=0.5, there is a 57% chance that one can find an insertion of 50 bps. This implies that high coverage is desirable. In order to find a 1000 bp long insertion, approximately 25× base coverage by perfect reads is desired. Typically, at an error rate of 5%, only about a quarter of all 25-base reads are perfect and thus about 100× base coverage may be desired which is within reach of AB SOLiD sequencing technology.

In summary, the mini-assembly for insertions is likely to be successful in finding an insertion if one exists and the assembly is also a helpful indication if an insertion exists and is real. In various embodiments an implied assumption is that the insertion detected is significantly smaller than the average distance between paired reads. One final challenge in detecting insertions is that frequently an insertion is a duplication of the existing genome (it is possible that most insertions are duplications). For this class of insertions, one can further divide it into two types: one is the case in which the insertion is a duplication of another region far away from the inserted place (>6 kp away, e.g., jumping gene). For this type, the approach and analysis described above works well. Using pairing information, one can separate reads that cover the two duplicated regions and then the insertion is novel in its neighborhood of about 6 K bp.

Software Implementation for Finding Alignments with a Single Insertion or Deletion Earlier sections discussing the statistics of finding indels addressed finding the optimal alignment (minimum number of mismatches) with one insertion or one deletion. Here the size of the insertion or deletion was set to be smaller than certain user specified limits (insertions and deletions may have different limits). In this section, an efficient software implemented approach to finding such alignments is presented.

Given the following: let ins be the maximum size of an insertion, del be the maximum size of a deletion and nmis be the maximum number of mismatches allowed. Find the optimum alignment (with minimum number of mismatches) between a read and a substring of a region of the reference sequence, such that it has at most one deletion smaller than del OR one insertion with size smaller than ins but not both, AND the number of mismatches is at most nmis.

Discussed is an approach for finding the best alignment with one deletion. The best alignments with one insertion can be found similarly. In one aspect the idea is to find gap-free alignments for each flanking sequence. Defining top-half alignments as gap-free alignments starting from the one portion of a flanking region and bottom-half alignments start at the other portion of a flanking region. One may note that an alignment with one deletion is a joining of one top-half and one bottom-half alignment.

To present the data analysis approach, an abstract data structure is introduced referred to as a dominating list of half alignments. If A and B are two top-half alignments with the same number of mismatches and they are at flanking regions a and b, respectively, call B dominating A if and only if a<b and B is longer that A. For any set of half alignments X with the same number of mismatches, a dominating subset of X includes all half alignments h in X such that no other half alignment in X dominates h. Design a dynamic data structure called dominating list S which maintains the dominating subset of a dynamic set of half alignments with a fixed number of mismatches.

S supports three operations: (1) insertion where a new top-half alignment is inserted to the set; (2) findmin which return the longest alignment in the set; and (3) deletemin which removes the longest alignment in S. Note that insert will also remove some alignments in the set which are dominated by the new alignment. The below discussion describes the approach using this abstract data type and then give an efficient implementation of it that gives a linear time algorithm of the total number of half alignments.

The approach processes flanking regions from 1 to R. Let k=nmis, and maintain k+1 lists S0 . . . Sk for top alignments with 0 to k mismatches. At the time when processing flanking region j, store all the dominating top alignments at flanking regions<j and with i mismatches in Si. At flanking region j, find all the top alignments with up to k mismatches and insert them in the list with the correct number of mismatches. Also find all the bottom alignments with up to k mismatches and try to combine them with top half alignments in S to form an alignment with one deletion.

The outline of the approach is described in the following pseudocode:

---

Approach deletion:
1. Let S0, S1...,Sk be empty
2. For flanking region j =1 to R do
    a. For each top alignment A at flanking region j with m<=k mismatches do
        i. Insert it to Sm;
    b. For each Sp, repeat deletemin if the longest half alignments are too far away such that too large of a deletion will be introduced.
    c. For each bottom alignment B at flaking region j with m<=k mismatches do
        i. For p=0 to k-m do
            1. X=findmin(Sp);
            2. if length of X plus length of B is larger than read length
                a. report an alignment with m+p mismatches and then break (from the inner for loop);

---

Note that at step 2.c.i.2.a, report an alignment with one deletion. Keeping track of all the reported alignments and maintaining the one with the minimum number of mismatches at the end of the program, reports the best alignment.

Analysis of the Running Time

The running time comprises the time to compute all of the half alignments at steps 2.a and 2.c, and the time to process these alignments at steps 2.c.i and 2.a.i. For random sequences, the average time to find all top alignments or all bottom alignments of up to k mismatches depends on the average length of alignments with k mismatches (since on a flanking region to find half alignment with k mismatches must first find ones with 0, 1, . . . , k−1 mismatches) and is $O(4kR/3)=O(kR)$.

For a set of dominating top alignments, sorting the alignments by increasing flanking regions, the lengths of the alignments decrease. Processing alignments by flanking regions, the alignments are inserted in increasing order of flanking regions. An implementation of the data type Sj is to use a two-directional linked list ordered by flanking region. Then findmin and deletemin can be done in O(1) time. Insertion is performed by visiting the alignment from the back of the linked list and removing alignments with shorter length until either the head of the list is reached or one with a longer length is found. Since each alignment can be deleted once the total time on step 2.a.i is O(kR). Similarly, total time at step 2.b is O(kR).

It initially appears that the loop at 2.c.i takes O(k) time each, but since the length of the longest alignment of Sj decreases when j increases and step 2.c will visit at most k+1 alignments (one each with 0, 1, . . . , k mismatches) with increasing lengths, the whole step 2.c can be implemented as a merge between two ordered lists (by length) of k+1-item, so the total time on step 2.c is O(kR). Now the total time of the approach is O(kR). This compares favorably to O(LR) for traditional SW-type alignments (Smith and Waterman 1990, Needleman and Wunsh 1970) as noted that the typical value for k is 0-2 and L could be 30-50.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The systems, methods, and analytical approaches of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Although the disclosed teachings has been described with reference to various applications, methods, and compositions, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

What is claimed is:

1. A computer implemented method of nucleic acid sequence analysis, comprising:
    receiving first nucleic acid sequence information comprising one or more mate pair sequences, wherein mate pair sequences comprise a first non-overlapping pairwise sequence and a second non-overlapping pairwise sequence separated by an intervening sequence length;
    receiving second nucleic acid sequence information comprising at least one reference sequence;
    performing a computer assisted mapping operation for the mate pair sequences in which the first non-overlapping pairwise sequence and the second non-overlapping pairwise sequence for a respective mate pair are aligned to the at least one reference sequence using a processor by the steps of:
        performing a first mapping operation using a processor to align the first non-overlapping pairwise sequence of the mate pair sequences to the at least one reference sequence with a first selected mismatch constraint,
        identifying mate pair sequences having first non-overlapping pairwise sequences which are aligned to the at least one reference sequence while satisfying the selected mismatch constraint, designating a window region within the at least one reference sequence for the identified mate pair sequences based on the alignment of the first non-overlapping pairwise sequence to the at least one reference sequence, performing a second mapping operation using a processor to align the second non-overlapping pairwise sequence to the window region of the reference sequence with a second selected mismatch constraint, identifying mate pair sequences with first and second non-overlapping pairwise sequences that have mapped to the at least one reference sequence following performing the first and second mapping operations; and, outputting the results of the mapping operations.

2. The method of claim 1, wherein the second mapping operation further identifies indels with respect to the reference sequence by determining a difference between an expected intervening sequence length between the non-overlapping pairwise sequences and an observed intervening sequence length between the non-overlapping pairwise sequences.

3. The method of claim 2, wherein the indel comprises an insertion occurring between the non-overlapping pairwise sequences which accounts for the difference between the expected intervening sequence length and the observed intervening sequence length.

4. The method of claim 2, wherein the indel comprises a deletion occurring between the non-overlapping pairwise sequences which accounts for the difference between the expected intervening sequence length and the observed intervening sequence length.

5. The method of claim 1, wherein the first nucleic acid sequence information comprises paired read sequence information separated by the intervening sequence whose length is within a known range.

6. The method of claim 5, wherein each of the paired read sequences has a length of between approximately 10 and 75 bases.

7. The method of claim 5, wherein the intervening sequence has a length of between approximately 2 kilobases and 15 kilobases.

8. A system for nucleic acid sequence analysis, comprising:

a data analysis component implemented on a computing device configured to:

receive first nucleic acid sequence information for one or more mate pair sequences, wherein mate pair sequences comprise a first non-overlapping pairwise sequence and a second non-overlapping pairwise sequence separated by an intervening sequence length and further configured to receive second nucleic acid sequence information for at least one reference sequence;

perform a mapping operation for the mate pair sequences in which the first non-overlapping pairwise sequence and the second non-overlapping pairwise sequence for a respective mate pair are aligned to the at least one reference sequence by the steps of:

performing a first mapping operation aligning the first non-overlapping pairwise sequence of the mate pair sequences to the at least one reference sequence with a first selected mismatch constraint, identifying mate pair sequences having first non-overlapping pairwise sequences which are aligned to the at least one reference sequence while satisfying the selected mismatch constraint, designating a window region within the at least one reference sequence for the identified mate pair sequences based on the alignment of the first non-overlapping pairwise sequence to the at least one reference sequence, performing a second mapping operation to align the second non-overlapping pairwise sequence to the window region of the reference sequence with a second selected mismatch constraint, identify mate pair sequences with first and second non-overlapping pairwise sequences that have mapped to the at least one reference sequence following performing the first and second mapping operations; and, a data terminal for displaying the results of the mapping operations generated by the data analysis component to a user.

9. The system of claim 8, wherein the second mapping operation performed by the data analysis unit further identifies indels with respect to the reference sequence by determining a difference between an expected intervening sequence length between the non-overlapping pairwise sequences and an observed intervening sequence length between the non-overlapping pairwise sequences.

10. The system of claim 9, wherein the indel comprises an insertion occurring between the non-overlapping pairwise sequences which accounts for the difference between the expected intervening sequence length and the observed intervening sequence length.

11. The system of claim 9, wherein the indel comprises a deletion occurring between the non-overlapping pairwise sequences which accounts for the difference between the expected intervening sequence length and the observed intervening sequence length.

12. The system of claim 8, wherein the first nucleic acid sequence information comprises paired read sequence information separated by the intervening sequence whose length is within a known range.

13. The system of claim 12, wherein each of the paired read sequences has a length of between approximately 10 and 75 bases.

14. A non-transitory computer-readable medium, the computer-readable medium being readable to execute a method of nucleic acid sequence analysis, the method comprising:

receiving first nucleic acid sequence information comprising one or more mate pair sequences, wherein mate pair sequences comprise a first non-overlapping pairwise sequence and a second non-overlapping pairwise sequence separated by an intervening sequence length;

receiving second nucleic acid sequence information comprising at least one reference sequence;

performing a computer assisted mapping operation for the mate pair sequences in which the first non-overlapping pairwise sequence and the second non-overlapping pairwise sequence for a respective mate pair are aligned to the at least one reference sequence by the steps of:

performing a first mapping operation aligning the first non-overlapping pairwise sequence of mate pair sequences to the at least one reference sequence with a first selected mismatch constraint, identifying mate pair sequences having first non-overlapping pairwise sequences which are aligned to the at least one reference sequence while satisfying the selected mismatch constraint, designating a window region within the at least one reference sequence for the mate pair sequences based on the alignment of the first non-overlapping pairwise sequence to the at least one reference sequence, performing a second mapping operation to align the second non-overlapping pairwise sequence to the window region of the reference sequence with a second selected mismatch constraint, identifying mate pair sequences with first and second non-overlapping pairwise sequences that have mapped to the at least one reference sequence following performing the first and second mapping operations;

and, outputting the results of the mapping operations.

15. The computer-readable medium of claim 14, wherein the second mapping operation further identifies indels with respect to the reference sequence by determining a difference between an expected intervening sequence length between the non-overlapping pairwise sequences and an observed intervening sequence length between the non-overlapping pairwise sequences.

16. The computer-readable medium of claim 15, wherein the indel comprises an insertion occurring between the non-overlapping pairwise sequences which accounts for the difference between the expected intervening sequence length and the observed intervening sequence length.

17. The computer-readable medium of claim 15, wherein the indel comprises a deletion occurring between the non-overlapping pairwise sequences which accounts for the difference between the expected intervening sequence length and the observed intervening sequence length.

18. The computer-readable medium of claim 14, wherein the first nucleic acid sequence information comprises paired read sequence information separated by the intervening sequence whose length is within a known range.

19. The computer-readable medium of claim 18, wherein each of the paired read sequences has a length of between approximately 10 and 75 bases.

20. The computer-readable medium of claim 19, wherein the intervening sequence has a length of between approximately 2 kilobases and 15 kilobases.

* * * * *